(12) United States Patent
Sathaye et al.

(10) Patent No.: US 10,903,612 B1
(45) Date of Patent: Jan. 26, 2021

(54) DOCK DEVICE WITH INTEGRATED CLAMP

(71) Applicant: AMAZON TECHNOLOGIES, INC., Seattle, WA (US)

(72) Inventors: Maya Shirish Sathaye, Seattle, WA (US); Ippei Matsumoto, Daly City, CA (US); Manish Avinash Mantrawadi, Redmond, WA (US); Douglas W. Moskowitz, Bellevue, WA (US)

(73) Assignee: AMAZON TECHNOLOGIES, INC., Seattle, WA (US)

( * ) Notice: Subject to any disclaimer, the term of this patent is extended or adjusted under 35 U.S.C. 154(b) by 0 days.

(21) Appl. No.: 16/453,703

(22) Filed: Jun. 26, 2019

(51) Int. Cl.
| H01R 33/18 | (2006.01) |
| H05K 5/02 | (2006.01) |
| H05K 5/00 | (2006.01) |
| H01R 33/76 | (2006.01) |
| H01R 13/52 | (2006.01) |
| H02J 7/00 | (2006.01) |
| H01R 13/502 | (2006.01) |
| A61B 5/024 | (2006.01) |

(52) U.S. Cl.
CPC .......... *H01R 33/18* (2013.01); *H01R 13/502* (2013.01); *H01R 13/5219* (2013.01); *H01R 33/7685* (2013.01); *H02J 7/0042* (2013.01); *H05K 5/0086* (2013.01); *H05K 5/0226* (2013.01); *H05K 5/0247* (2013.01); *A61B 5/02438* (2013.01); *A61B 2560/0214* (2013.01); *A61B 2560/0456* (2013.01)

(58) Field of Classification Search
CPC .... A61B 2500/0456; A61B 2560/0456; A61B 2560/0468; A61B 2560/0481; A61B 2560/0487; H01R 33/18; H01R 13/502; H01R 13/5219; H02J 7/0042
USPC ....... 439/283, 467, 822, 687, 696, 695, 731, 439/816, 819, 837–839, 843, 846, 506, 439/728, 729, 759, 31, 372, 237, 238, 439/806, 341, 446, 534, 104, 294; 320/115

See application file for complete search history.

(56) References Cited

U.S. PATENT DOCUMENTS

| 4,449,772 A | * | 5/1984 | Johnson, III | ........... H01R 11/24 439/504 |
| 5,205,739 A | * | 4/1993 | Malo | ...................... H01R 12/62 439/66 |
| 5,407,368 A | * | 4/1995 | Strand | .................... H01R 11/24 439/729 |

(Continued)

*Primary Examiner* — Harshad C Patel
(74) *Attorney, Agent, or Firm* — Lindauer Law, PLLC

(57) ABSTRACT

A dock includes a first section and a second section joined with a spring hinge assembly. An applied force opens the dock and a device may be placed within the dock. The first section includes a first concavity which approximately conforms to a top surface of the device. Within the first concavity is a ridge which comes into contact with part of the top surface of the device. The second section includes a second concavity within which a bottom surface of the device fits. Electrical contacts such as pogo pins within the second section come into contact with electrical contacts on the bottom surface of the device. Annular elastomeric features around at least some of the pogo pins have a top edge which may come into contact with the bottom surface of the device. The spring hinge applies a force that closes the dock, retaining the device therein.

20 Claims, 8 Drawing Sheets

(56) References Cited

U.S. PATENT DOCUMENTS

| | | | | |
|---|---|---|---|---|
| 5,452,180 | A * | 9/1995 | Register | G06F 1/1632 361/679.44 |
| 5,454,739 | A * | 10/1995 | Strand | A61B 5/0416 439/729 |
| 5,569,041 | A * | 10/1996 | Sonobe | H01R 13/639 439/157 |
| 6,042,414 | A * | 3/2000 | Kunert | H01R 13/6272 248/310 |
| 6,560,101 | B1 * | 5/2003 | Oross | G06F 1/1632 361/679.43 |
| 6,638,092 | B2 * | 10/2003 | Groebe | H01R 12/725 439/341 |
| 8,376,303 | B2 * | 2/2013 | Yang | F16M 11/22 248/146 |
| 9,325,087 | B2 * | 4/2016 | Chawla | H01R 12/88 |
| 9,632,536 | B1 * | 4/2017 | Kuo | G06F 1/1632 |
| 10,250,051 | B2 * | 4/2019 | Hopkins | H02J 7/0044 |
| 2004/0115994 | A1 * | 6/2004 | Wulff | H04R 13/2471 439/700 |
| 2006/0061958 | A1 * | 3/2006 | Solomon | G06F 1/1632 361/679.43 |
| 2006/0171112 | A1 * | 8/2006 | Lev | G06F 1/162 361/679.27 |
| 2006/0250764 | A1 * | 11/2006 | Howarth | G06F 1/1632 361/679.41 |
| 2007/0070598 | A1 * | 3/2007 | Chuang | G06F 1/1632 361/679.43 |
| 2008/0239658 | A1 * | 10/2008 | Chou | G06F 1/1632 361/679.38 |
| 2011/0095724 | A1 * | 4/2011 | Byrne | G11B 33/122 320/115 |
| 2011/0117833 | A1 * | 5/2011 | Hong | G06F 1/1632 455/3.06 |
| 2013/0050932 | A1 * | 2/2013 | Williams | G06F 1/1632 361/679.41 |
| 2014/0069710 | A1 * | 3/2014 | Webb | H05K 7/14 174/549 |
| 2015/0026957 | A1 * | 1/2015 | Onishi | B22D 23/10 29/527.5 |
| 2015/0036283 | A1 * | 2/2015 | Suckle | G06F 1/1632 361/679.43 |
| 2015/0116927 | A1 * | 4/2015 | Robinson | G06F 1/1632 361/679.43 |
| 2015/0280337 | A1 * | 10/2015 | Chawla | H01R 12/721 439/59 |
| 2015/0357749 | A1 * | 12/2015 | Brunner | A61N 1/3752 361/752 |
| 2016/0091925 | A1 * | 3/2016 | Ardisana, II | G06F 1/1632 361/679.43 |
| 2017/0153667 | A1 * | 6/2017 | Suckle | G06F 1/1632 |
| 2017/0344060 | A1 * | 11/2017 | Shibayama | G06F 1/1616 |

* cited by examiner

DOCK DEVICE WITH INTEGRATED CLAMP

BACKGROUND

A portable electronic device, such as a wearable device, may have a rechargeable battery that requires recharging.

BRIEF DESCRIPTION OF FIGURES

The detailed description is set forth with reference to the accompanying figures. In the figures, the left-most digit(s) of a reference number identifies the figure in which the reference number first appears. The use of the same reference numbers in different figures indicates similar or identical items or features.

Figure 1:
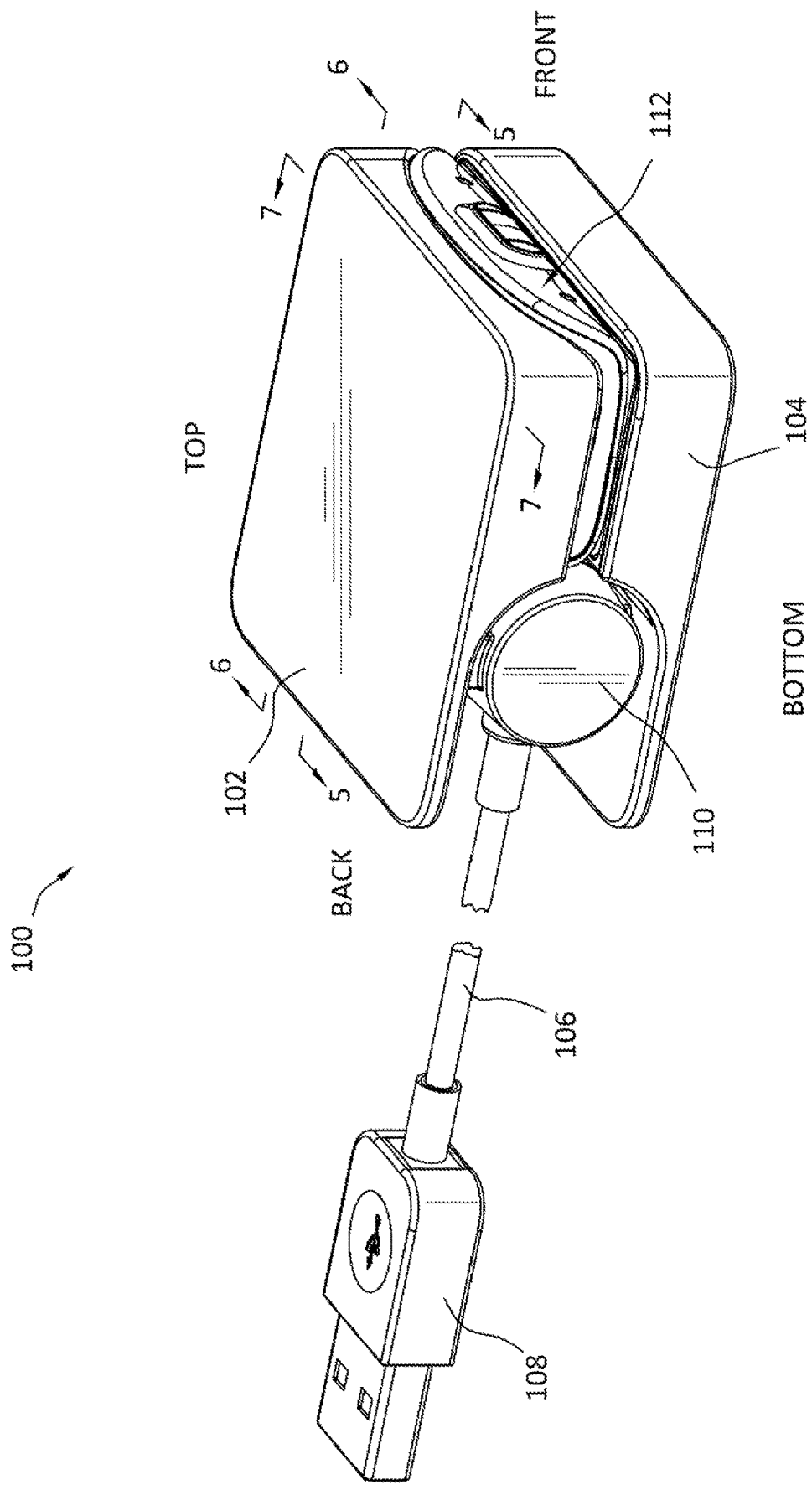
FIG. 1 illustrates a dock device with integrated clamp in a closed position with a wearable device emplaced, according to one implementation.

While implementations are described herein by way of example, those skilled in the art will recognize that the implementations are not limited to the examples or figures described. It should be understood that the figures and detailed description thereto are not intended to limit implementations to the particular form disclosed but, on the contrary, the intention is to cover all modifications, equivalents, and alternatives falling within the spirit and scope as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean "including, but not limited to".

The structures depicted in the following figures are not necessarily according to scale. Furthermore, the proportionality of one component to another may change with different implementations. In some illustrations the scale or a proportionate size of one structure may be exaggerated with respect to another to facilitate illustration, and not necessarily as a limitation.

DETAILED DESCRIPTION

Portable electronic devices, such as a wearable device, are used in a variety of situations and rely on electrical power during operation. For example, a user may wear a wearable device. The wearable device may present information to the user, acquire data about the user's physical condition such as pulse rate, physical movement, and so forth.

The wearable device may include a physical form factor or external shape that facilitates wear. In one implementation, the wearable device may comprise a housing within which the electronics are mounted and a band which retains the housing to the user. For example, the wearable device may have a form factor similar to a wristwatch. The external shape of the wearable device may include one or more curves. These curves may facilitate wear, improve comfort, avoid sharp edges that could be uncomfortable for the user, and so forth. For example, a top portion of the housing may be convexly curved, while a bottom portion of the housing that comes into contact with the user during wear exhibits one or more curves.

The electrical power used during operation of the wearable device may be provided by a battery, capacitor, or other energy storage device. The energy storage device may be recharged from an external source. Traditional techniques may use a plug from an external power source that is inserted into a jack on the wearable device to provide electrical power to the wearable device. This electrical power may then be used to recharge the energy storage device in the wearable device. However, the jack and plug combination exhibits several disadvantages. For example, the jack in the wearable device either increases the overall volume of the wearable device or removes that volume for use by other components such as a battery. In another example, the jack may be prone to intrusion by contaminants such as sweat, dirt, and so forth.

Other traditional arrangements of providing electrical conductivity to a wearable device involve the use of contacts. For example, the weight of the wearable device may be used to maintain a connection between contacts on the wearable device and contacts in a cradle. One arrangement relies on the weight of the wearable device to maintain contact and is prone to inadvertent disconnection. Another arrangement relies on a particular external shape of the wearable device to mechanically engage external contacts.

Described in this disclosure is a dock that provides for reliable and persistent electrical contact with an electronic device, such as a wearable device. The dock includes a clamping mechanism and various features that mechanically retain the wearable device while establishing a persistent electric connection. The dock may be designed to engage an electronic device with a wide range of external shapes, including various curves, bands, and so forth.

The dock may have a first section and a second section that are joined by a hinge. For example, the first section may be on top while the second section is on bottom. A biasing mechanism, such as a spring, applies a biasing force that brings the front of the sections together. The sections may be shaped to allow the wearable device to fit within. During use, an external force is applied which opens the dock and the electronic device is inserted between the sections. The external force is removed, and the biasing mechanism clamps down on the electronic device. For example, a user may press on a portion of the first section to open the dock, insert the wearable device between the sections, and stop pressing, closing the dock.

A first feature within the first section provides physical contact between the first section and a top portion of the electronic device. For example, the first feature may comprise a ridge of elastomeric material. The first feature provides a defined area that is in contact with the electronic device, allowing the electronic device to shift or rotate as needed to fully engage the contacts in the second section and establish a reliable electric connection for charging.

The second section may include electrical contacts used to establish an electrical connection with the electronic device. For example, the second section may have a recess, and within the recess may be two or more spring-biased electrical contacts, such as pogo pins, leaf spring contacts, and so forth. During use, the biasing force pushes down on the electronic device, providing an affirmative connection between the spring-biased electrical contacts and electrical contacts on a bottom surface of the electronic device.

In some implementations an elastomeric feature may be arranged around one or more of the electrical contacts in the second section. For example, the elastomeric feature may comprise a ring or annulus around a pogo pin. During use, the biasing force pushes the bottom surface of the electronic device into the elastomeric feature. As a top portion of the elastomeric feature comes into contact with the bottom surface of the electronic device, contaminants such as water, sweat, dirt, and so forth may be pushed aside. The displacement of contaminants by the elastomeric feature(s) prevents an undesired conductive pathway between the electrical contacts in the second section. For example, the elastomeric features prevent shorting between the pogo pins due to sweat on the bottom surface of the electronic device.

The dock may include a second feature that enforces placement of the electronic device in a particular orientation. For example, the second feature may comprise a ridge that extends away from a body of a hinge assembly. The second feature does not obstruct the electronic device when the electronic device is properly oriented with regard to the dock, but if incorrectly installed the second feature mechanically obstructs and prevents the electronic device from being seated. This prevents the electronic device from being placed in the dock but not establishing an electric connection that could prevent charging.

By providing a clamping action between the sections using the hinge and the biasing mechanism, the dock is able to support the wearable device in different configurations or implementations. For example, the compliance afforded by the clamping action allows for the same dock to accommodate a wearable device to be inserted with a band attached, without the band attached, different models that may have different thicknesses, and so forth.

The dock may include other mechanical features to maintain the electronic device between the first and second section during use. For example, the second section may have a recess with a lip around a perimeter of the recess. The lip may mechanically engage a portion of the electronic device, limiting lateral movement of the electronic device while the electronic device is in the dock.

The dock described in this disclosure provides several advantages. These include, but are not limited to: a compact overall size, ability to operate with electronic devices which may vary in exterior shape or size, ability to prevent short circuits due to contaminants on the electronic device, the ability to maintain a reliable and persistent electrical connection, the ability to mitigate situations involving incorrect orientation of the electronic device with respect to the dock, and so forth.

While the dock is described as providing electrical power for charging an energy storage device in the electronic device, other functions may also be provided. For example, the dock may be used to establish a wired or physical communication connection with the electronic device for data transfer, diagnostic, or other purposes.

Illustrative System

FIG. 1 illustrates a dock device 100 (dock), according to one implementation. The dock 100 comprises a first section 102 and a second section 104. A cable 106 extends from the second section 104 and is terminated with a connector 108. For example, the connector 108 may comprise a universal serial bus (USB) type "A" plug. In some implementations visible indicia may be present on one or more of the first section 102 or the second section 104. For example, a logo may be printed on an upper surface of the first section 102, allowing a user to more easily determine the orientation of the dock 100. In other implementations other indicia may be presented. For example, the exterior shape of a portion of the first section 102 may be rounded or extend upwards, providing a visual and tactile indication of the orientation of the dock 100. In another example, the outer surface of the first section 102 may be smooth while the outer surface of the second section 104 that would come into contact with a surface upon which the dock 100 rests during use may comprise an elastomeric or nonskid material. A hinge 110 joins the first section 102 and the second section 104. The hinge 110 allows the first section 102 and the second section 104 to move relative to one another. A biasing mechanism, such as a spring, magnet, and so forth applies a biasing force between the sections. The biasing force serves to bring a first front portion of the first section 102 towards a second front portion of the second section 104.

In the implementation depicted here, the hinge 110 includes the biasing mechanism, such as a spring, that applies the biasing force. In another implementation the biasing mechanism may be separate from the hinge 110. For example, a first magnet may be affixed to the first section 102 and a second magnet may be affixed to the second section 104. Attraction between the two magnets may operate as the biasing mechanism and provide the biasing force.

An external force may be applied to open the dock 100, increasing the distance between the first front portion of the first section 102 and the second front portion of the second section 104. For example, a user may press down on a first back portion of the first section 102 that is located behind the hinge 110, rotating the top section 102 with respect to the hinge 110. In another example, the user may pinch, applying pressure simultaneously and in opposite directions to the first back portion of the first section 102 and a second back portion of the second section 104 that is located behind the hinge 110. This pinch may also cause the dock 100 to open. When the external force is removed, the biasing mechanism closes the dock 100.

In this illustration, an electronic device 112 (device) is depicted within the dock 100. One implementation of the device 112 is described in more detail with regard to FIG. 8. In the closed configuration shown here, the biasing force from the biasing mechanism is transferred mechanically from the first section 102 to a top surface of the device 112. Likewise, the biasing force from the biasing mechanism is transferred mechanically from the second section 104 to a bottom surface of the device 112. The dock 100 thus clamps or applies pressure to the device 112, affirmatively maintaining the device 112 within the dock 100. Because the first section 102 and the second section 104 may be moved relative to one another under the urging of the biasing mechanism, the dock 100 is able to accommodate different configurations of the device 112. For example, the device 112 may comprise a wearable device that is retained against a user during wear with a band. The dock 100 is able to accommodate the band (not shown) by providing clearance for the band between the first section 102 and the second section 104 while the device 112 is in the dock 100.

The dock 100 is also able to accommodate different models of the device 112. For example, overall thickness of different models may vary or the external shape of a housing of different models may vary. Because the first section 102 and the second section 104 may be moved relative to one another under the urging of the biasing mechanism, the dock 100 is able to accommodate these variations. This allows the dock 100 to be used with different devices 112.

Figure 5:
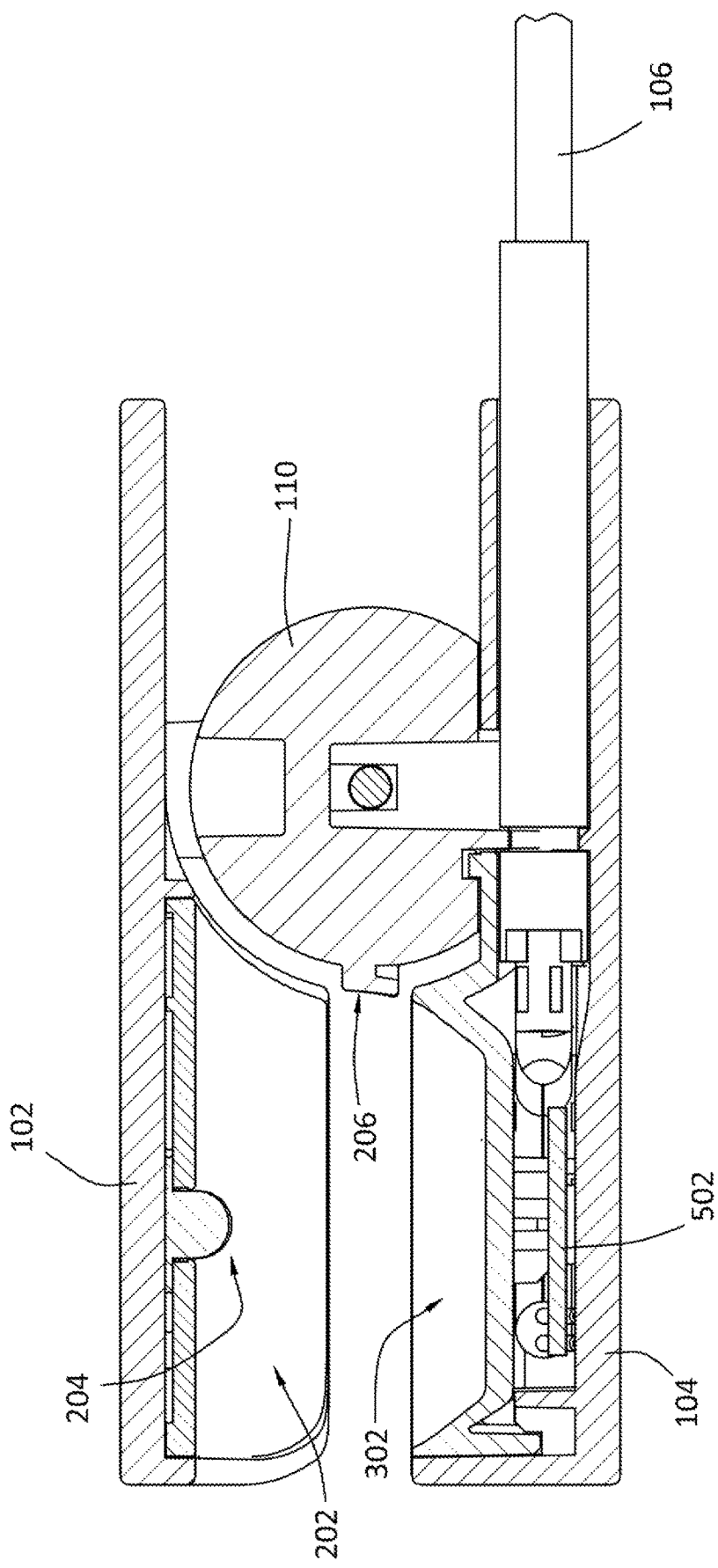
FIG. 5 depicts a cross section of the implementation shown in FIG. 1 along a plane extending front to back.
Figure 6:
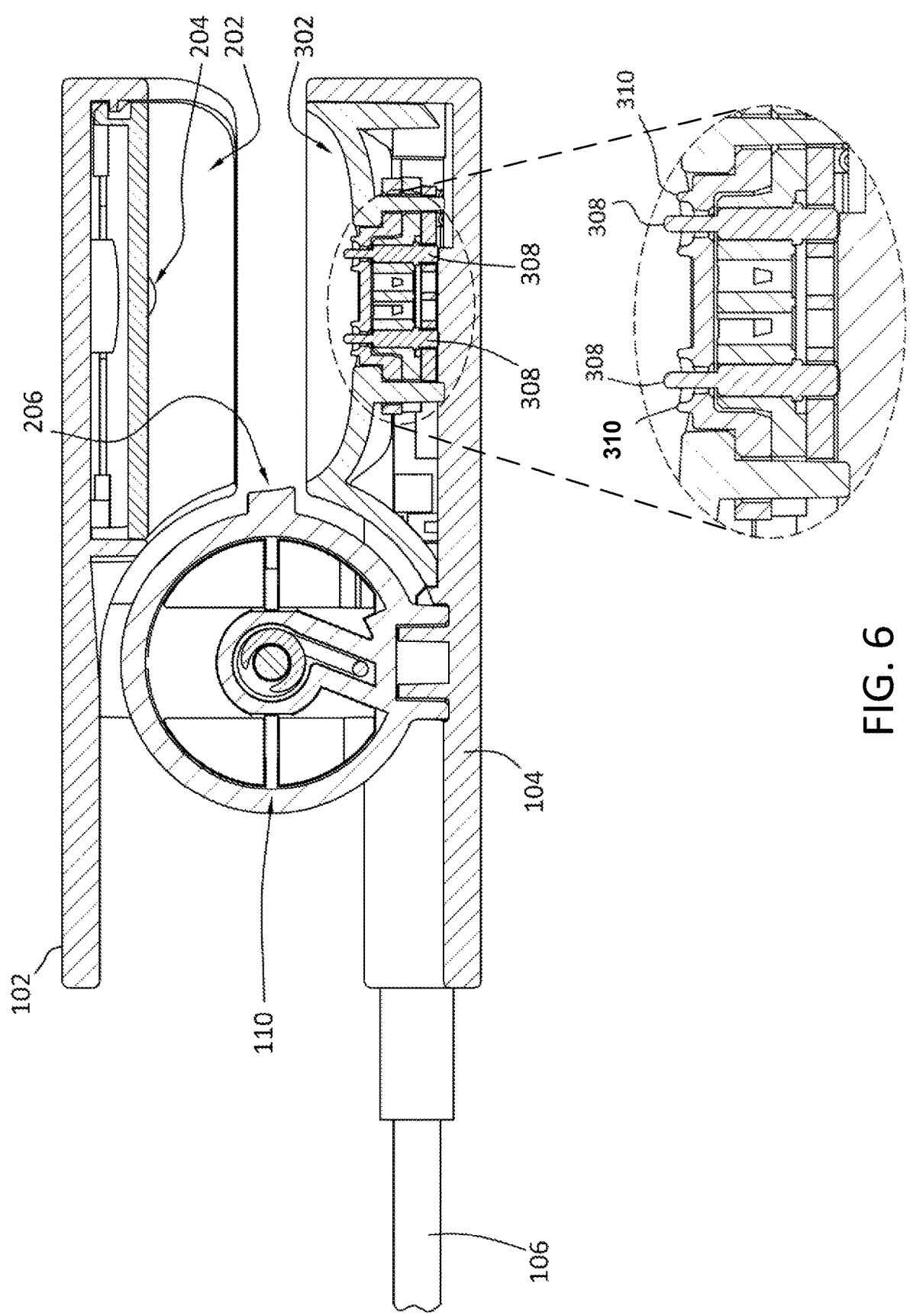
FIG. 6 depicts a cross section of the implementation shown in FIG. 1 along a plane extending front to back through the electrical contacts.
Figure 7:
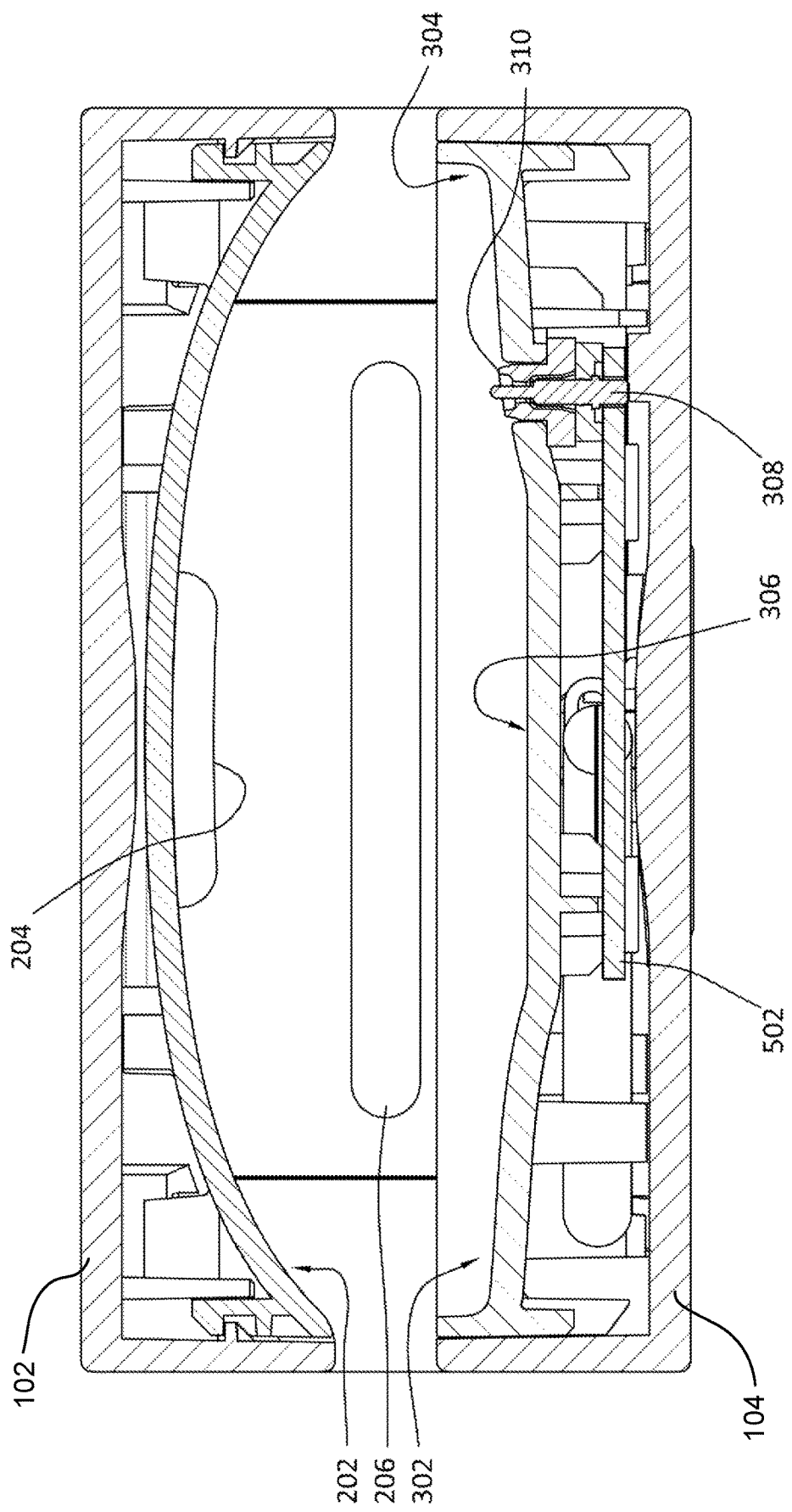
FIG. 7 depicts a cross section of the implementation shown in FIG. 1 along a plane extending left to right.

The following figures include cross sections along the various lines indicated herein. For example, FIG. 5 depicts a cross section along line 5-5, FIG. 6 depicts a cross section along line 6-6, and FIG. 7 depicts a cross section along line 7-7.

Figure 2:
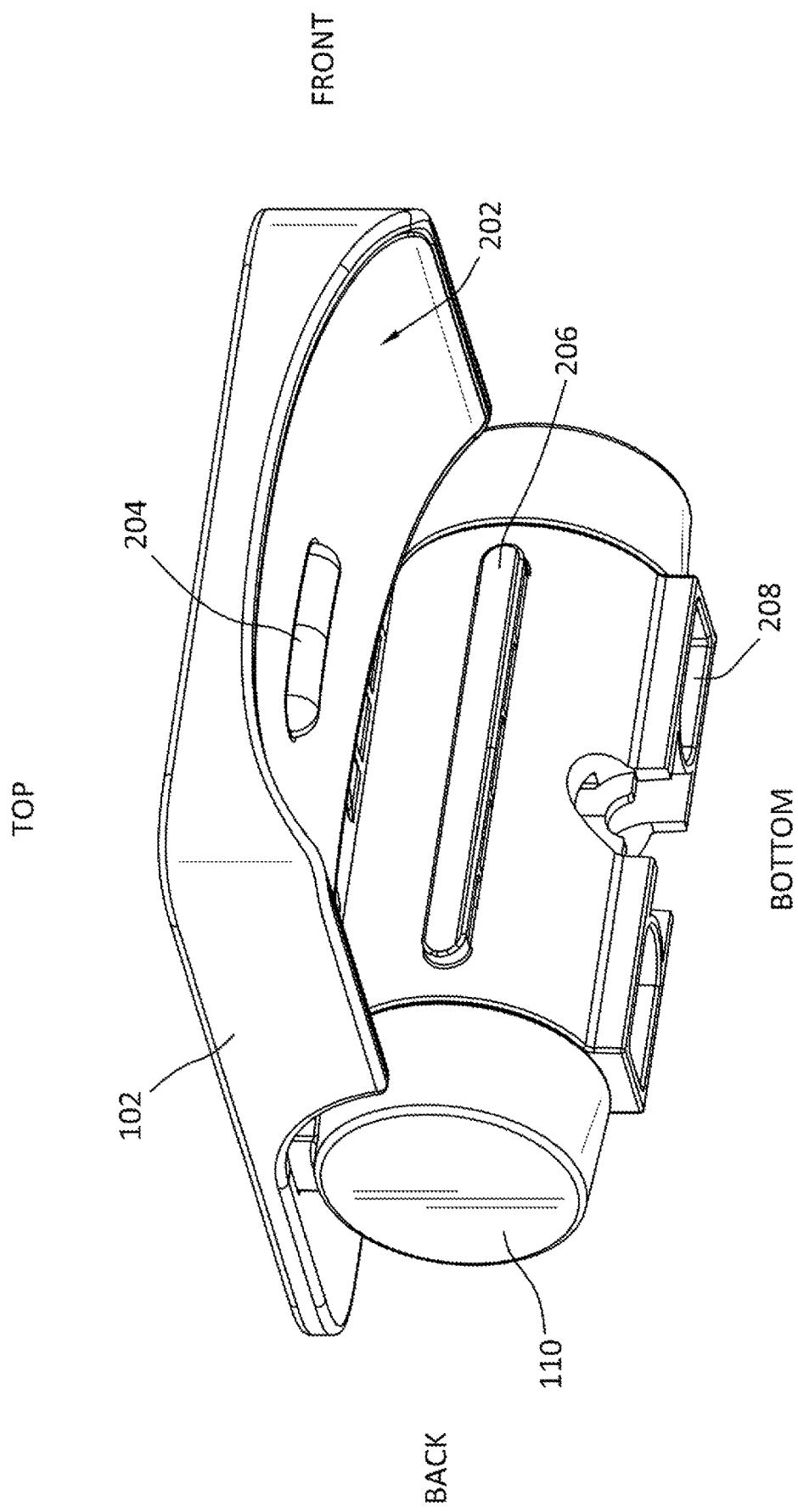
FIG. 2 depicts a first section of the dock device which includes a contact feature in a first recess and a key feature extending from a hinge assembly, according to one implementation.

FIG. 2 depicts the first section 102 of the dock 100 and the hinge 110, according to one implementation. In this view, a first recess 202 in the first section 102 opens downwards or generally toward the second section 104. The first recess 202 may be generally concave, with the concavity opening downwards or towards the second section 104. The overall shape of the first recess 202 is configured to fit or accommodate at least a portion of a top of the device 112 when the device 112 is present.

The interior of the first recess 202 comprises a first inner surface. One or more features 204 may extend away from the first inner surface. In the implementation depicted here, a first feature 204 comprises a ridge that extends away from the first inner surface. The first feature 204 is arranged in a linear ridge having a long axis that is parallel to a long axis of the first recess 202. For example, the linear ridge of the first feature 204 extends from left to right with respect to the dock 100. In other implementations one or more other types of features 204 may be used. For example, the first feature 204 may comprise a hemisphere or dome that extends away from the first inner surface.

In some implementations the one or more features 204 may comprise an elastomeric material. For example, the elastomeric material may comprise a silicone rubber. During use, the biasing force provided by the biasing mechanism is transferred from the first section 102 to the one or more features 204 to a top surface of the device 112.

Also shown is a second feature 206 that extends away from a body of the hinge 110. The second feature 206 is located between the first recess 202 and a second recess in the second section 104. The second feature 206 may comprise a linear ridge having a long axis that is parallel to a long axis of the first recess 202. The linear ridge may extend from proximate to a left end of the body of the hinge 110 to proximate to a right end of the hinge 110. In other implementations, the second feature 206 may comprise other shapes or arrangements. For example, the second feature 206 may comprise a hemisphere. In another example, a plurality of features 206 may be used.

The second feature 206 extends towards the front of the dock 100. The size and placement of the second feature 206 is configured to complement the external shape of the device 112. The second feature 206 may enforce a particular orientation of the device 112 with respect to the dock 100 during use. For example, the second feature 206 is sized so as to not obstruct the device 112 when the device 112 is properly oriented with regard to the dock 100, but if incorrectly installed the second feature 206 mechanically obstructs and prevents the device 112 from being seated in the dock 100. Continuing the example, the device 112 may have a button on a first side to accept user input. In the proper orientation the button may be visible at the front of the dock 100, while an improper orientation may place the button towards the back of the dock 100. This obstruction provided by the interaction of the button on the device 112 and the second feature 206 in the improper orientation prevents proper seating of the device 112 with respect to the dock 100. This provides immediate and apparent feedback to the user that the device 112 is improperly oriented, allowing the user the opportunity to move the device 112 to the proper orientation. Once in the proper orientation, the dock 100 may establish an electric connection with the device 112 to allow for charging, data transfer, and so forth.

The hinge 110 may include one or more mounting features 208 that facilitate joining the hinge 110 to the second section 104. The hinge 110 may be joined to one or more of the first section 102 or the second section 104 using various techniques. For example, mechanical fasteners, mechanical interference fits, adhesives, welding, and so forth may be used to join the first section 102 and the second section 104 to the hinge 110. In another implementation the hinge 110 may comprise a living hinge and at least a portion of the first section 102 and the second section 104 may be a unitary piece.

A first front section extends from a line through a long axis of the hinge 110 towards a front of the first section 102. A first back section extends from the line towards a back of the first section 102.

Figure 3:
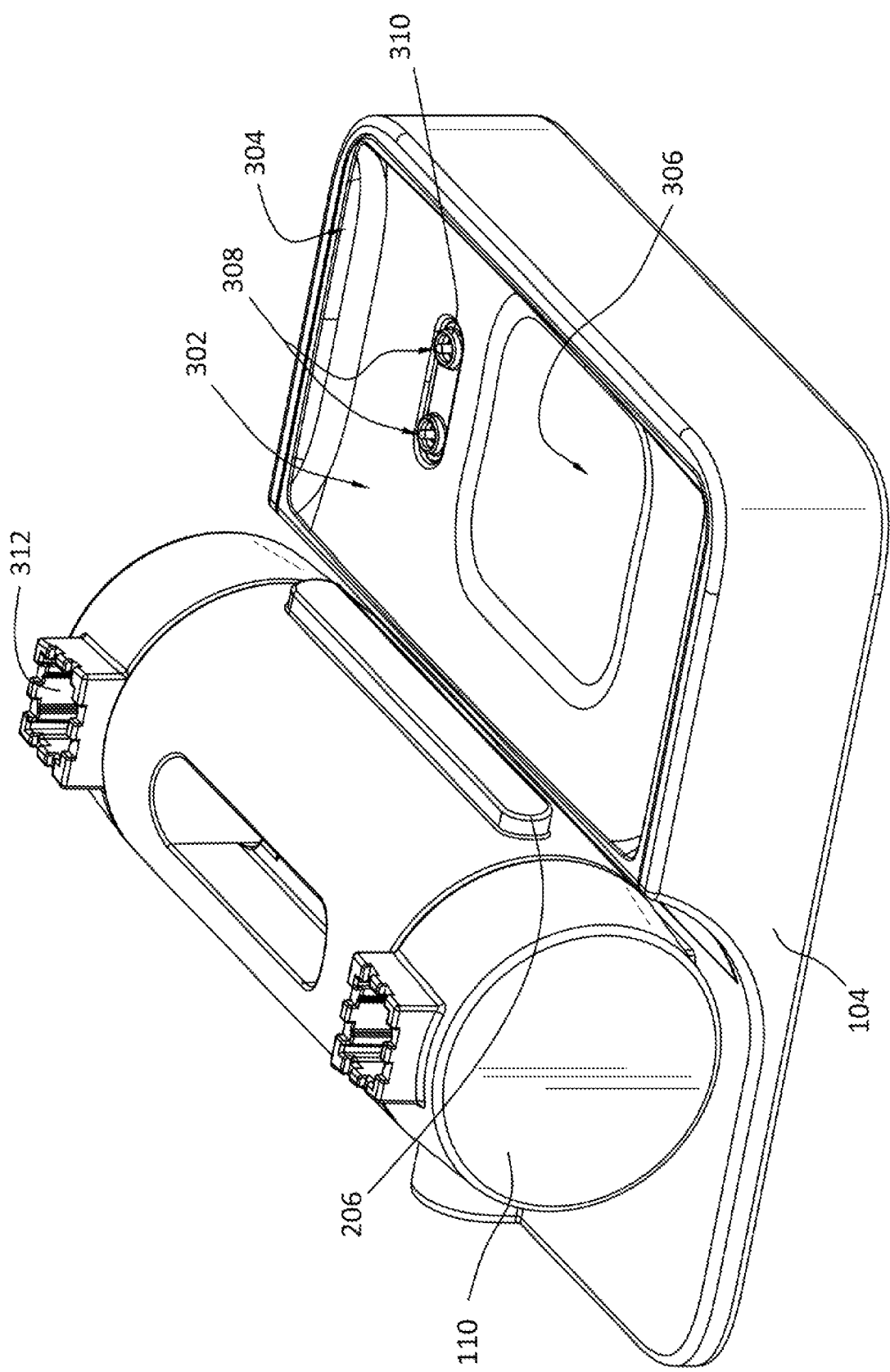
FIG. 3 depicts a second section of the dock device which includes a second recess having two electrical contacts and the key feature extending from the hinge assembly, according to one implementation.

FIG. 3 depicts the second section 104 of the dock 100, according to one implementation. The second section 104 may comprise a second recess 302. The second recess 302 may be generally concave, with the concavity opening upwards or towards the first section 102. The overall shape of the second recess 302 is configured to fit or accommodate at least a portion of a bottom of the device 112 when the device 112 is present.

The interior of the second recess 302 comprises a second inner surface. One or more lips 304 or edges may be present around at least a portion of the perimeter of the second recess 302. For example, a first lip 304 may be present at a first end of the second recess 302 and a second lip 304 may be present at a second end of the second recess 302 as shown here. The lips 304 may constrain lateral movement of the device 112 when the device 112 is present. For example, the first lip 304 and the second lip 304 may come into contact with a ridge or other feature on the device 112, preventing the device 112 from slipping left or right while the dock 100 is closed.

A third recess 306 or other feature may be present within the second inner surface of the second recess 302. For example, the third recess 306 may accommodate a bottom portion of the device 112.

One or more electrical contacts 308 are present in the second recess 302. In the implementation depicted here, there are two electrical contacts 308 arranged between a first edge of the third recess 306 and a first end of the second recess 302. The one or more electrical contacts 308 may comprise pogo pins that extend through the second inner surface. The pogo pin includes a spring-biased contact which comes into contact with a corresponding pad or electrical contact on the device 112 when the device 112 is present. The end of the pogo pin or other electrical contact 308 may extend beyond the second inner surface. For example, when uncompressed, the pin in the pogo pin may be "proud" or extend slightly above the second inner surface and into the second recess 302.

In one implementation the electrical contact 308 that is closest to a front edge of the second section 104 may be connected to an electrical ground. In this implementation, during insertion of the device 112, the device 112 may come into contact with the electrical ground first, grounding the device 112 to the dock 100 or the electronics therein. This grounding may reduce the likelihood of arcing during insertion of the device 112.

One or more elastomeric features 310 may be arranged around one or more of the electrical contacts 308. For example, an elastomeric feature 310 comprising a ring of elastomeric material centered on a pogo pin is shown here. While a ring is shown, in other implementations other shapes may be used. For example, a linear feature may be arranged between the pogo pins, having a long axis perpendicular to a line through the two pogo pins and extending beyond the second inner surface.

During use of the dock 100, the biasing force from the biasing mechanism pushes the bottom surface of the device 112 into the elastomeric feature(s) 310. As a top portion of the elastomeric feature 310 comes into contact with the bottom surface of the device 112, contaminants such as water, sweat, dirt, and so forth on the bottom surface of the device 112 may be pushed aside. The displacement of contaminants by the elastomeric feature(s) 310 prevents or reduces an undesired conductive pathway between the electrical contacts 308 in the second section 104. For example, the elastomeric features 310 prevent an electrical short circuit between the pogo pins due to sweat on the bottom surface of the device 112.

The hinge 110 may include one or more mounting features 312 that facilitate joining the hinge 110 to the first section 102.

Also visible is the second feature 206 that extends away from a body of the hinge 110.

A second front section extends from a line through a long axis of the hinge 110 towards a front of the second section 104. A second back section extends from the line towards a back of the second section 104.

Figure 4:
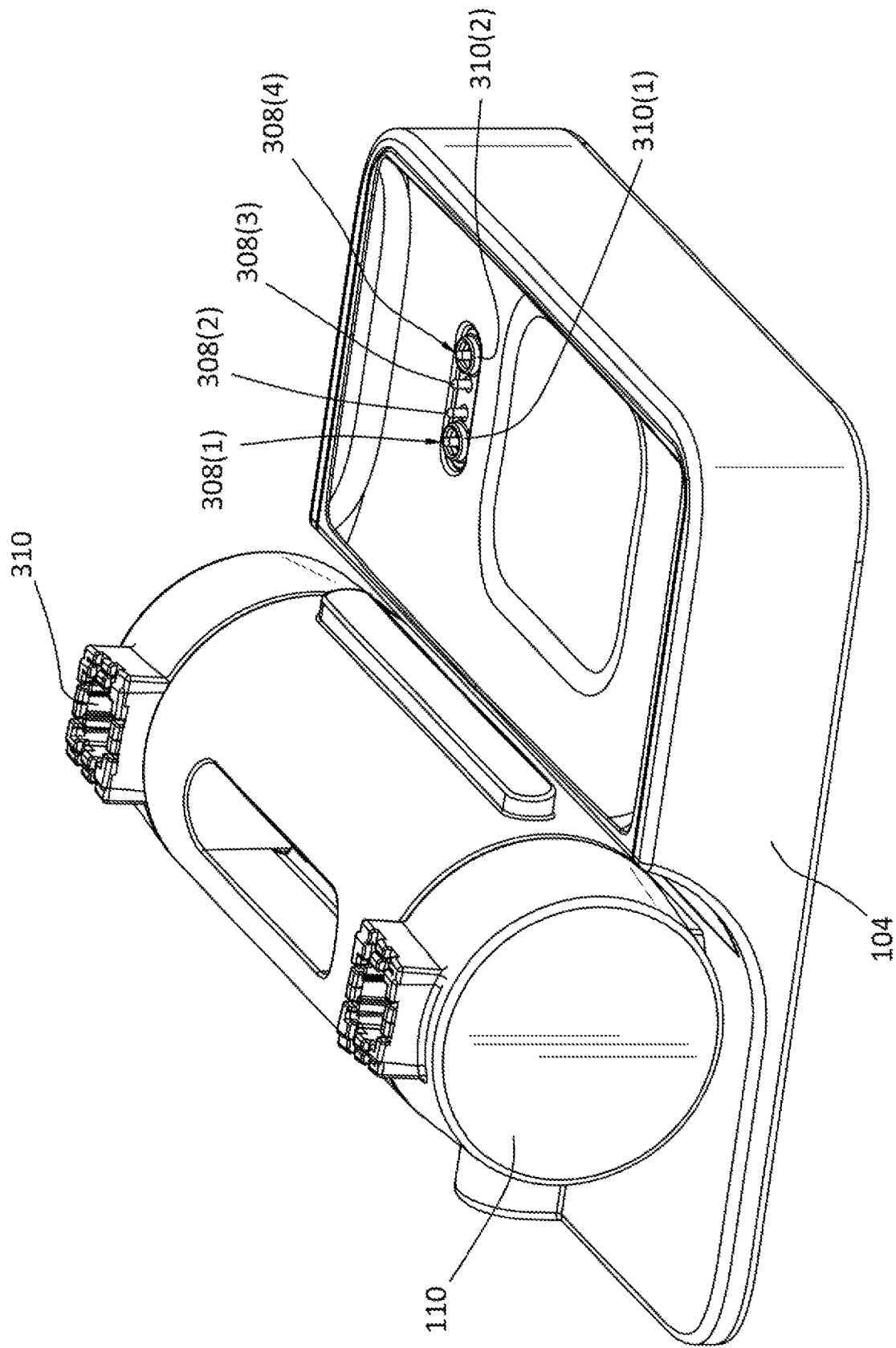
FIG. 4 depicts another implementation of the second section of the dock device which includes a second recess having four electrical contacts and the key feature extending from the hinge assembly, according to another implementation.

FIG. 4 depicts another implementation of the second section 104 of the dock 100. This implementation includes a total of four electrical contacts 308, compared to the two electrical contacts 308 shown in FIG. 3. In some implementations, additional electrical contacts may be used to provide increased power transfer, for data communication, and so forth. Shown here are a first pogo pin 308(1), a second pogo pin 308(2), a third pogo pin 308(3), and a fourth pogo pin 308(4). A first elastomeric feature 310(1) is arranged around the first pogo pin 308(1). As described above, a top portion of the first elastomeric feature 310(1) extends beyond the second inner surface into the second recess 302.

The second pogo pin 308(2) extends beyond the second inner surface. The third pogo pin 308(3) also extends beyond the second inner surface.

The fourth pogo pin 308(4) extends beyond the second inner surface. A second elastomeric feature 310(2) is arranged around the fourth pogo pin 308(4). A top portion of the second elastomeric feature 310(2) extends beyond the second inner surface. In the implementation depicted here, the pogo pins are arranged in a linear arrangement. For example, contact points of the first pogo pin 308(1), the second pogo pin 308(2), the third pogo pin 308(3), and the fourth pogo pin 308(4) are arranged in a line. In other implementations, other arrangements may be used.

In this implementation the elastomeric features 310 are not present on the center two pogo pins 308(2) and 308(3). In other implementations, one or more of the electrical contacts 308 may have a corresponding elastomeric feature 310.

FIG. 5 depicts a cross section along line 5-5 of the implementation shown in FIG. 1. In this view the dock 100 is shown in the closed configuration. The device 112 is omitted for clarity. The first section 102 is shown, along with the first feature 204. In this implementation, the first feature 204 comprises a ridge with a rounded profile extending into the first recess 202.

Also visible is the second feature 206 extending from the body of the hinge 110 towards the front of the dock 100.

The second section 104 is also shown, with the second recess 302 visible. Circuitry 502 is also depicted in the second section 104. For example, the circuitry 502 may comprise a circuit board which includes power control circuitry, a USB interface, upon which the electrical contacts 308 are mounted, and so forth. For example, the circuitry 502 may connect, via the cable 106, to an external power source. In some implementations the circuitry 502 may operate to control when the electrical contacts 308 are energized. For example, the circuitry 502 may measure a predetermined resistance between two or more electrical contacts 308. Based on the measured resistance, the circuitry 502 may operate to provide electrical power to the electrical contacts 308.

FIG. 6 depicts a cross section along line 6-6 of the implementation shown in FIG. 1. In this view the dock 100 is shown in the closed configuration. The device 112 is omitted for clarity. The first section 102 is shown, along with the first feature 204. In this implementation, the first feature 204 comprises a ridge with a rounded profile extending into the first recess 202.

Also visible is the second feature 206 extending from the body of the hinge 110 towards the front of the dock 100.

The second section 104 is also shown, with the second recess 302 visible. This cross section passes through the electrical contact 308. In the implementation depicted here, the electrical contacts 308 comprise pogo pins. An enlarged view shows the pins of the pogo pins 308 extending beyond the second inner surface of the second recess 302. The elastomeric features 310 are also shown, with a top portion of these features extending beyond the second inner surface of the second recess 302 as well.

When the device 112 is in the dock 100, the biasing force provided by the biasing mechanism urges the first front section of the first section 102 toward the second front section of the second section 104. This clamping action provides a force which, transmitted through the first feature 204 and into the housing of the device 112, pushes a bottom surface of the device 112 into the second recess 302. This force places electrical contacts on a bottom surface of the device 112 into contact with the pogo pins 308. The force provided by the spring in the spring-biased pogo pins 308 affirmatively maintains contact between the pin and the electrical contact of the device 112. Meanwhile, the top portion of the elastomeric features 310 is pressed into the bottom surface of the device 112, which may displace contaminants present on the bottom surface. This displacement reduces or eliminates the likelihood of the contaminants providing an electrically conductive short circuit between the electrical contacts 308.

FIG. 7 depicts a cross section along line 7-7 of the implementation shown in FIG. 1. In this view the dock 100 is shown in the closed configuration. The device 112 is omitted for clarity. The first section 102 is shown, along with the first feature 204 which extends from the first inner surface into the first recess 202 and runs from left to right along the first inner surface.

Also visible is the second feature 206 extending from the body of the hinge 110 towards the front of the dock 100.

The second section 104 is also shown, with the second recess 302 visible. The stepped nature of the second recess 302 is apparent. Also visible are the lips 304 of the second recess 302. Within the second recess 302 the third recess 306 is shown. One of the electrical contacts 308 with corresponding elastomeric feature 310 is shown. Also visible is the circuitry 502.

Figure 8:
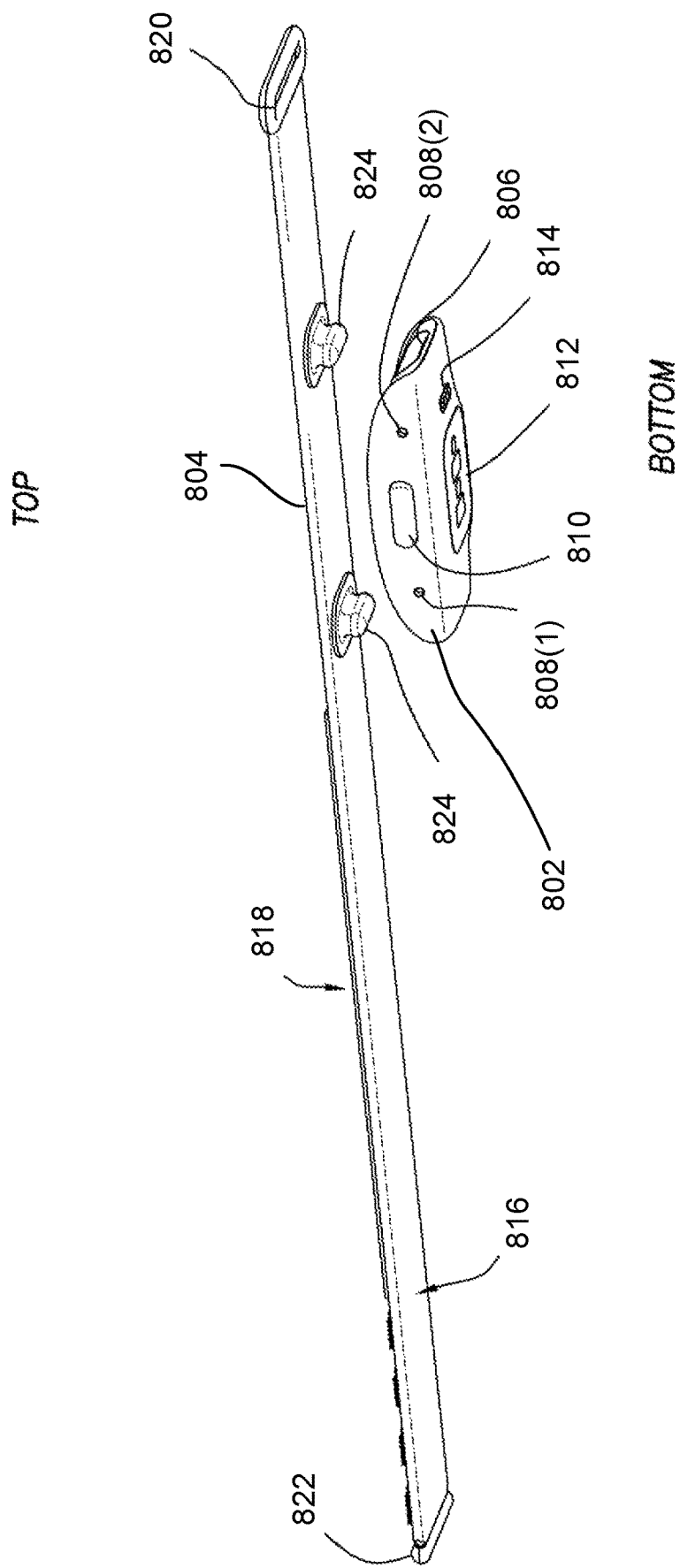
FIG. 8 is an illustrative wearable device that may be retained by the dock, according to one implementation.

FIG. 8 is a device 112 that may be retained by the dock 100, according to one implementation. For example, the dock 100 may be used to provide electrical power that charges a rechargeable battery within the device 112.

The device 112 may comprise a wearable device with a housing 802 and a band 804. The housing 802 may comprise a body and an upper cover (not visible). The body, upper cover, and other components may comprise one or more of a metal, plastic, composite, ceramic, and so forth.

The body may include one or more openings. For example, during assembly components may be placed within the body through an opening that is then closed by the upper cover. The body and the upper cover may be joined such that the resulting housing 802 is sealed. In the implementation shown here, a top surface of the housing 802 is curved. During wear, the top surface of the housing 802 faces away from the portion of the user to which the device 112 is retained. A bottom surface of the housing 802 is proximate to the portion of the user. For example, at least a portion of the bottom surface may be in contact with the user while the device 112 is being worn.

The body includes one or more receptacles 806. As illustrated here, the body is generally rectangular when viewed from above, with two ends. In the implementation depicted here a first receptacle 806 is proximate to a first end of the body while a second receptacle 806 is proximate to a second end of the body. Each receptacle 806 has an opening on the top surface of the housing 802. For example, the receptacle 806 may be within the body while the upper cover includes apertures for each of the openings of the receptacles 806.

Each receptacle 806 is configured such that the opening or entry to the receptacle 806 is smaller along at least one dimension than an interior volume of the receptacle 806. For example, each receptacle 806 may include a retention ridge that is proximate to the opening in the receptacle 806. The retention ridge introduces a constriction or narrowing. For example, in cross-section the receptacle 806 may appear to resemble a mushroom shape with a root or stalk that is narrower than a larger, bulbous tip. In some implementations the retention ridge may extend along the entire perimeter of the opening.

The housing 802 may include one or more apertures 808. The body may include several apertures 808 for microphone ports, light emitting diodes, air pressure sensors, and so forth. In this view, apertures 808(1) and 808(2) are shown on a first side of the housing 802. For example, the aperture 808(1) may comprise a pressure equalization port and the aperture 808(2) may provide a port for a microphone to receive sound from outside the housing 802.

A button 810 is also present on this side of the housing 802 between the apertures 808(1) and 808(2). The button 810 may be used to activate a switch to allow for user input. The button 810 may extend away from a side of the housing 802. In the event of an misorientation of the device 112 within the dock 100, at least a portion of the second feature 206 would come into contact with at least a portion of the button 810 or associated portion of the housing 802. The obstruction posed by the second feature 206 prevents insertion of the device 112 in an improper orientation.

A sensor window 812 is arranged on a bottom surface of the housing 802. The sensor window 812 may be transparent to one or more wavelengths of light. For example, the sensor window 812 may be transparent to visible and infrared light. The sensor window 812 may be used by one or more sensors to obtain information about the user. A field of view of one or more sensors may pass through the sensor window 812. For example, an optical heart rate monitor may comprise a light emitting diode (LED) or other light source that emits light which passes through the sensor window 812 and to the arm of the user. Reflected or scattered light returns through the sensor window 812 where it is measured by a photodetector. In another example a camera may have a field of view that passes through the sensor window 812 to obtain images of a portion of the user's arm.

In some implementations, the portion of the bottom surface of the housing 802 that includes the sensor window 812 may protrude away from the remainder of the bottom surface, as shown here.

One or more electrical contacts 814 may also be present on the bottom surface of the housing 802. The electrical contacts 814 may be used to transfer data, provide electrical power, and so forth. In some implementations the electrical contacts 814 may be recessed with respect to the bottom surface of the device 112. In other implementations the electrical contacts 814 may be flush with or extend slightly from the bottom surface of the device 112. When the device 112 is installed in the dock 100 in the proper orientation, the electrical contacts 308 of the dock 100 come into contact with corresponding electrical contacts 814 in the device 112.

The band 804 may comprise a flexible member having a first end and a second end. The flexible member includes an inner surface 816 and an outer surface 818. When the band 804 is affixed to the housing 802, at least a part of the inner surface 816 of the flexible member is proximate to the top surface of the housing 802.

The flexible member may comprise one or more of fabric, an elastomeric material, a plurality of links, and so forth. For example, the flexible member may comprise an elastic fabric. A loop 820 may be arranged at the first end of the flexible member while an endcap 822 is arranged at the second end. The loop 820 may be a rigid loop. For example, the loop 820 may comprise metal that is encased in plastic. In other implementations, the loop 820 may comprise a flexible material.

One or more protrusions 824 extend away from the inner surface of the flexible member. In the implementation shown here, a first protrusion 824 extends from the inner surface of the flexible member at a first location L1 and a second protrusion 824 extends from the inner surface at a second location L2.

Each protrusion 824 is configured to maintain mechanical engagement after insertion into the receptacle 806. A portion of each protrusion 824 is larger than the narrowest part of the opening into the receptacle 806. The protrusions 824 may comprise an elastomeric material. In one implementation, the protrusions 824 may comprise silicone rubber having a hardness as measured using a durometer with a Shore A reading of between 70 and 90.

Each protrusion 824 is aligned to a respective receptacle 806 and a force is applied to the flexible member on the outer surface 818 opposite the protrusion 824. The applied force causes the enlarged portion of the protrusion 824 to temporarily deform, allowing it to pass into the cavity of the receptacle 806. Once within the receptacle 806, the elastomeric material expands, securing part of the protrusion 824 within the receptacle 806. The band 804 is now affixed to the housing 802.

With the housing 802 and the band 804 attached, the device 112 may be worn by a user. The flexible member may include on the outer surface 818 a loop portion comprising a plurality of loops and a hook portion comprising a plurality of hooks. To affix the device 112 to the user, the second end of the flexible member having the endcap 822 is passed through the loop 820. The user may place their forearm into the loop formed by the flexible member. The second end of the flexible member may then be pulled such that the inner surface is in comfortable contact with the user's forearm, and the hook portion is then pressed against the loop portion, securing the flexible member.

In other implementations, other mechanisms may be used to secure the device 112 to the user. For example, the flexible member may utilize a buckle, a folding clasp, butterfly closure, and so forth. In another example, the flexible member may comprise a contiguous loop of elastomeric material, allowing the user to pass their hand through the loop which then contracts to hold the device 112 in place.

In some implementations the housing 802 may include one or more output devices on the top surface. For example, a display device may be arranged on the top surface between the receptacles 806 to provide visual output to the user. At least a portion of the flexible member that is between the first location L1 and the second location L2 may be transparent, or may contain one or more holes or another opening to allow at least a portion of the display device to be visible. For example, the flexible member may comprise a transparent material such as silicone rubber. In another example, the flexible member may comprise an opening or aperture that is coincident with the display device. In another example, the flexible member may comprise a plurality of holes, perforations, or spaces between threads that allow at least a portion of light from the display device to pass through.

In other implementations the dock 100 may be modified to operate in conjunction with devices 112 of other external shapes. For example, the size and profiles of one or more of the first recess 202, second recess 302, first feature 204, and second feature 206 may be varied to fit other devices 112.

Specific physical embodiments as described in this disclosure are provided by way of illustration and not necessarily as a limitation. Those having ordinary skill in the art readily recognize that alternative implementations, variations, and so forth may also be utilized in a variety of devices, environments, and situations. Although the subject matter has been described in language specific to structural features or methodological acts, it is to be understood that the subject matter defined in the appended claims is not necessarily limited to the specific features or acts described. Rather, the specific features, structures, and acts are disclosed as exemplary forms of implementing the claims.

Processes discussed herein may be implemented in hardware, software, or a combination thereof. In the context of software, the described operations represent computer-executable instructions stored on one or more non-transitory computer-readable storage media that, when executed by one or more processors, perform the recited operations. Generally, computer-executable instructions include routines, programs, objects, components, data structures, and the like that perform particular functions or implement particular abstract data types. Those having ordinary skill in the art will readily recognize that certain steps or operations illustrated in the figures above may be eliminated, combined, or performed in an alternate order. Any steps or operations may be performed serially or in parallel. Furthermore, the order in which the operations are described is not intended to be construed as a limitation.

Embodiments may be provided as a software program or computer program product including a non-transitory computer-readable storage medium having stored thereon instructions (in compressed or uncompressed form) that may be used to program a computer (or other electronic device) to perform processes or methods described herein. The computer-readable storage medium may be one or more of an electronic storage medium, a magnetic storage medium, an optical storage medium, a quantum storage medium, and so forth. For example, the computer-readable storage media may include, but is not limited to, hard drives, optical disks, read-only memories (ROMs), random access memories (RAMs), erasable programmable ROMs (EPROMs), electrically erasable programmable ROMs (EEPROMs), flash memory, magnetic or optical cards, solid-state memory devices, or other types of physical media suitable for storing electronic instructions. Further, embodiments may also be provided as a computer program product including a transitory machine-readable signal (in compressed or uncompressed form). Examples of transitory machine-readable signals, whether modulated using a carrier or unmodulated, include, but are not limited to, signals that a computer system or machine hosting or running a computer program can be configured to access, including signals transferred by one or more networks. For example, the transitory machine-readable signal may comprise transmission of software by the Internet.

Separate instances of these programs can be executed on or distributed across any number of separate computer systems. Thus, although certain steps have been described as being performed by certain devices, software programs, processes, or entities, this need not be the case, and a variety of alternative implementations will be understood by those having ordinary skill in the art.

Additionally, those having ordinary skill in the art will readily recognize that the techniques described above can be utilized in a variety of devices, environments, and situations. Although the subject matter has been described in language specific to structural features or methodological acts, it is to be understood that the subject matter defined in the appended claims is not necessarily limited to the specific features or acts described. Rather, the specific features and acts are disclosed as illustrative forms of implementing the claims.

What is claimed is:

1. A system comprising:
   a dock comprising:
      a top section comprising:
         a first back portion,
         a first front portion comprising a first recess that opens downwards, wherein the first recess has a first inner surface, and
         a contact feature comprising a first ridge that extends downwards from the first inner surface;
      a bottom section comprising:
         a second back portion,
         a second front portion comprising a second recess that opens upwards, wherein the second recess has a second inner surface, a first lip at a first end of the second recess, and a second lip at a second end of the second recess, a third recess within the second inner surface,
a first pogo pin and a second pogo pin that are located between a first edge of the third recess and the first end of the second recess, and
circuitry to provide electrical power to the first pogo pin and the second pogo pin; and
a spring hinge assembly that joins the top section and the bottom section, wherein the spring hinge assembly applies a biasing force to bring the first front portion towards the second front portion.

2. The system of claim 1, further comprising:
a second ridge that extends away from a body of the spring hinge assembly towards a front of the dock and is arranged between the first recess and the second recess.

3. The system of claim 1, further comprising:
a wearable device comprising:
a second top section that is convex, wherein the first recess conforms to the second top section and the biasing force is applied to the second top section by the contact feature;
a second bottom section, wherein the second recess and the third recess conform to the second bottom section; and
a first electrical contact and a second electrical contact on the second bottom section, wherein the first electrical contact comes into contact with the first pogo pin and the second electrical contact comes into contact with the second pogo pin.

4. A device comprising:
a first section comprising:
a first front portion comprising a first recess having a first inner surface, and
a first feature that extends away from the first inner surface;
a second section comprising:
a second front portion comprising a second recess having a second inner surface, wherein the first inner surface is opposite the second inner surface;
a first pogo pin that extends through the second inner surface;
a second pogo pin that extends through the second inner surface;
circuitry to provide electrical power to the first pogo pin and the second pogo pin; and
a spring hinge assembly that joins the first section and the second section, wherein the spring hinge assembly applies a biasing force to bring the first front portion towards the second front portion.

5. The device of claim 4, wherein the first feature comprises an elastomeric material arranged in a linear ridge having a long axis that is parallel to a long axis of the first recess.

6. The device of claim 4, further comprising:
a second feature comprising a ridge that extends away from a body of the spring hinge assembly and is arranged between the first recess and the second recess.

7. The device of claim 4, further comprising:
a first elastomeric feature arranged around the first pogo pin, wherein the first elastomeric feature extends beyond the second inner surface; and
a second elastomeric feature arranged around the second pogo pin, wherein the second elastomeric feature extends beyond the second inner surface.

8. The device of claim 4, further comprising:
a first lip at a first end of the second recess;
a second lip at a second end of the second recess; and
wherein the second recess has a long axis that extends from the first end to the second end.

9. The device of claim 4, further comprising:
a third pogo pin that extends through the second inner surface; and
a fourth pogo pin that extends through the second inner surface.

10. The device of claim 4, further comprising:
a first elastomeric feature arranged around the first pogo pin, wherein the first elastomeric feature extends beyond the second inner surface;
a third pogo pin that extends through the second inner surface;
a fourth pogo pin that extends through the second inner surface;
a second elastomeric feature arranged around the second pogo pin, wherein the second elastomeric feature extends beyond the second inner surface; and
wherein the first pogo pin, the second pogo pin, the third pogo pin, and the fourth pogo pin are arranged in a line with the first pogo pin on a first end of the line, the second pogo pin on a second end of the line, and the third pogo pin and the fourth pogo pin located along the line between the first pogo pin and the second pogo pin.

11. A device comprising:
a first section comprising:
a first front portion having a first inner surface, and
a first feature that extends away from the first inner surface;
a second section comprising:
a second front portion comprising a first recess having a second inner surface, wherein the first recess has a concave shape opening toward the first section; and
at least one electrical contact;
a hinge that joins the first section and the second section, wherein the hinge has a rotational axis and the first front portion pivots about the rotational axis to move the first front portion toward and away from the second front portion; and
a biasing mechanism that applies a biasing force to bring the first front portion towards the second front portion.

12. The device of claim 11, wherein the first inner surface is within a second recess in the first front portion, and wherein the second recess has a concave shape opening toward the second section.

13. The device of claim 11, wherein the at least one electrical contact comprises at least one pogo pin that extends through the second inner surface.

14. The device of claim 11, wherein the at least one electrical contact comprises a pogo pin; and
further comprising an elastomeric feature arranged around the pogo pin, wherein the elastomeric feature extends beyond the second inner surface.

15. The device of claim 11, wherein:
the at least one electrical contact comprises a first pogo pin, a second pogo pin, a third pogo pin, and a fourth pogo pin;
the first pogo pin extends beyond the second inner surface;
a first elastomeric feature is arranged around the first pogo pin, wherein the first elastomeric feature extends beyond the second inner surface;
the second pogo pin extends beyond the second inner surface;

the third pogo pin extends beyond the second inner surface;

the fourth pogo pin extends beyond the second inner surface;

a second elastomeric feature is arranged around the fourth pogo pin, wherein the second elastomeric feature extends beyond the second inner surface; and contact points of the first pogo pin, the second pogo pin, the third pogo pin, and the fourth pogo pin are arranged in a line.

16. The device of claim 11, wherein the first feature comprises an elastomeric material arranged in a linear ridge having a long axis that is parallel to a long axis of the first recess.

17. The device of claim 11, wherein only the first feature comes into contact with an inserted device responsive to the biasing force.

18. The device of claim 11, further comprising:
a second feature comprising a ridge that extends away from a housing of the hinge and is arranged between the first section and the second section.

19. The device of claim 11, further comprising:
a first lip at a first end of the first recess; and
a second lip at a second end of the first recess;
wherein the first recess has a long axis that extends from the first end to the second end.

20. The device of claim 11, further comprising:
circuitry to provide electrical power to the at least one electrical contact.

* * * * *